(12) United States Patent
Kim et al.

(10) Patent No.: US 10,945,705 B2
(45) Date of Patent: Mar. 16, 2021

(54) PORTABLE ULTRASONIC FACILITIES DIAGNOSIS DEVICE

(71) Applicant: SM INSTRUMENT CO., LTD., Daejeon (KR)

(72) Inventors: Young Ki Kim, Daejeon (KR); YoungMin Kim, Daejeon (KR); JeaSun Lee, Daejeon (KR); Kwang Hyun Lee, Daejeon (KR); Seong Joo Han, Gyeonggi-do (KR); Jung Hyun Lim, Chungcheongnam-do (KR)

(73) Assignee: SM INSTRUMENT CO., LTD., Daejeon (KR)

( * ) Notice: Subject to any disclaimer, the term of this patent is extended or adjusted under 35 U.S.C. 154(b) by 265 days.

(21) Appl. No.: 15/807,981

(22) Filed: Nov. 9, 2017

(65) Prior Publication Data

US 2018/0333135 A1 Nov. 22, 2018

(30) Foreign Application Priority Data

May 16, 2017 (KR) .......................... 10-2017-0060394
May 16, 2017 (KR) .......................... 10-2017-0060422

(51) Int. Cl.
*A61B 8/00* (2006.01)
*G01S 15/89* (2006.01)
(Continued)

(52) U.S. Cl.
CPC .......... *A61B 8/4427* (2013.01); *A61B 8/4411* (2013.01); *A61B 8/462* (2013.01);
(Continued)

(58) Field of Classification Search
CPC ........ G01S 3/8086; G01S 5/22; G01S 15/899; A61B 8/4427; A61B 8/4411; A61B 8/54; A61B 8/462
See application file for complete search history.

(56) References Cited

U.S. PATENT DOCUMENTS 5,615,675 A * 4/1997 O'Donnell ......... G01N 29/0681
600/425
6,633,658 B1 * 10/2003 Dabney ............... G01S 7/52026
382/128

(Continued)

FOREIGN PATENT DOCUMENTS

KR 101477755 12/2014

*Primary Examiner* — Bo Joseph Peng
(74) *Attorney, Agent, or Firm* — IPLA P.A.

(57) ABSTRACT

A portable facility failure diagnosis device using detection of radiation ultrasonic waves, comprising: an ultrasonic sensor array; a data acquisition board (DAQ board) in which an electronic circuit for acquiring ultrasonic signals at a sampling frequency of the ultrasonic signals sensed by the ultrasonic sensor array is mounted on a substrate of the data acquisition board (DAQ board); a main board in which an operation processing device that processes the ultrasonic signals received from the DAQ board is mounted on the substrate and the processed ultrasonic sound source information to a display device; a data storage medium storing data processed in the operation processing device of the main board; a display device visually displaying the data processed; and an optical camera picking up an image of a direction.

9 Claims, 4 Drawing Sheets

(51) Int. Cl.
*G01S 3/808* (2006.01)
*G01S 5/22* (2006.01)

(52) U.S. Cl.
CPC .............. *A61B 8/54* (2013.01); *G01S 3/8086* (2013.01); *G01S 5/22* (2013.01); *G01S 15/899* (2013.01)

(56) References Cited

U.S. PATENT DOCUMENTS

| | | | | |
|---|---|---|---|---|
| 7,699,776 | B2* | 4/2010 | Walker | A61B 8/06 600/437 |
| 8,827,909 | B2* | 9/2014 | Kierulf | A61B 8/467 600/459 |
| 2001/0056240 | A1* | 12/2001 | Palti | A61B 5/417 600/481 |
| 2004/0215072 | A1* | 10/2004 | Zhu | A61B 5/0091 600/407 |
| 2007/0174152 | A1* | 7/2007 | Bjornberg | G01C 15/00 705/28 |
| 2013/0162796 | A1* | 6/2013 | Bharara | A61B 5/7425 348/77 |
| 2014/0160434 | A1* | 6/2014 | Brown, Jr. | A61B 3/0025 351/210 |
| 2015/0297177 | A1* | 10/2015 | Boctor | A61B 34/30 600/437 |

* cited by examiner

PORTABLE ULTRASONIC FACILITIES DIAGNOSIS DEVICE

BACKGROUND

This application claims priority to and the benefit of Korean Patent Application Nos. 10-2017-0060394 and 10-2017-0060422 each filed 16 May 2017 with the Korean Intellectual Property Office, the entire contents of which are incorporated herein by reference.

The present invention relates to a portable ultrasonic facilities diagnosis device capable of overlaying two or three images among an ultrasound image, an optical image, and a thermal image in a single screen, and particularly, to a portable ultrasonic facilities diagnosis device used for diagnosing a facility failure by not analyzing an echo-reflected ultrasonic wave with an ultrasonic wave transmitter and an ultrasonic wave receiver but showing a generation location of an ultrasonic wave (not an echo signal) naturally radiated from a machine or facility or a gas pipe as an image and further, showing the ultrasonic wave generation location in one screen through an image and the thermal image.

Patent Registration No. 10-1477755 provides a high-voltage board, a low-voltage board, a distribution board, and a motor control board equipped with an ultrasonic wave-based arc and corona discharge monitoring and diagnosing system which diagnoses a discharge state of arc or corona of a housing having the high-voltage board included therein, which include a sensor unit constituted by multiple ultrasonic sensors which contact or are installed proximate to a facility provided in the housing and which detect ultrasonic waves generated by the arc or corona discharge; and a monitoring device constituting an abnormality determining unit which senses arc or corona discharge generated in the facility and controls an internal state of the housing according to the sensed arc or corona discharge information, based on an ultrasonic signal detected by the sensor unit.

SUMMARY OF THE INVENTION

The present invention has been made in an effort to provide a portable ultrasonic facilities diagnosis device capable of overlaying two or three images among an ultrasound image, an optical image, and a thermal image in a single screen.

The present invention has been made in an effort to provide a portable ultrasonic facilities diagnosis device that visualizes an image for a generation location of an ultrasonic sound source naturally radiated by a mutual operation among components in a facility (apparatus), machines, etc. and a portable facility failure diagnosis device together with the thermal image and the optical image a computer program, unlike a medical ultrasonic diagnosing device visualizing an internal shape by a reflection wave after transmitting an ultrasonic wave by an ultrasonic apparatus in the related art.

In addition, the present invention has been made in an effort to provide a portable ultrasonic facilities diagnosis device which can realize sound in an ultrasonic wave region more efficiently than vibration sound which can diagnose an early fault in machinery failure diagnosis, and includes an ultrasound sensor, a processing device, a battery, a display device, and the like in one body case to allow a user to easily perform ultrasonic visualization while moving a measurement point, display the result to a visual display device together with the thermal image in real time, or enable the result to be recognized through an auditory display device.

In addition, the present invention has been made in an effort to provide a portable ultrasonic facilities diagnosis device which includes a program and an electronic means for forming an arithmetic processing step so as to be performed by the electronic means having appropriate performance and an arithmetic processing capability by optimizing and minimizing a data throughput (processing step) for visualization radiated ultrasonic waves without losing ultrasonic sound source location size information in an ultrasonic region where a data processing capacity is large to ultimately reduce the size and a weight of the apparatus, show excellent portability, and allows a user to visually or aurally recognize an ultrasonic wave visualization result on a spot in addition to the thermal image in real time, thereby showing excellent merchantability.

An exemplary embodiment of the present invention provides a portable facility failure diagnosis device using detection of radiation ultrasonic waves, including: an ultrasonic sensor array constituted by a plurality N of ultrasonic sensors and sensing ultrasonic signals radiated from a facility while orienting a radiation sound source; a data acquisition board in which an electronic circuit for acquiring ultrasonic signals $x_n$ at a sampling frequency $f_s$ of the ultrasonic signals sensed by the ultrasonic sensor array is mounted on a substrate of the data acquisition board; a main board in which an operation processing device that processes the ultrasonic signals received from the data acquisition board is mounted on the substrate and the processed ultrasonic sound source information to a display device; a data storage medium storing data processed in the operation processing device of the main board; a display device visually displaying the data processed by processed in the operation processing device of the main board; an optical camera picking up an image of a direction in which the ultrasonic sensor array is directed and transmitting the image to the main board; and an IR camera picking up a thermal image in a direction in which the optical camera is directed.

Further, the portable facility failure diagnosis device further includes an case internal charging battery or an external portable battery supplying power to the data acquisition board, the main board, and the display device and the ultrasonic sensor array, the data acquisition board, the main board, and the data storage medium are mounted and fixed on a plastic body case made of a hard material, and the main board overlaps and displays at least two to three images selected from ultrasonic sound source information, an optical image in a direction which the sensor array picked by the optical camera, and the thermal image picked by the IR camera together by matching location coordinates of the at least two to three images.

DETAILED DESCRIPTION OF THE INVENTION

Figure 1:
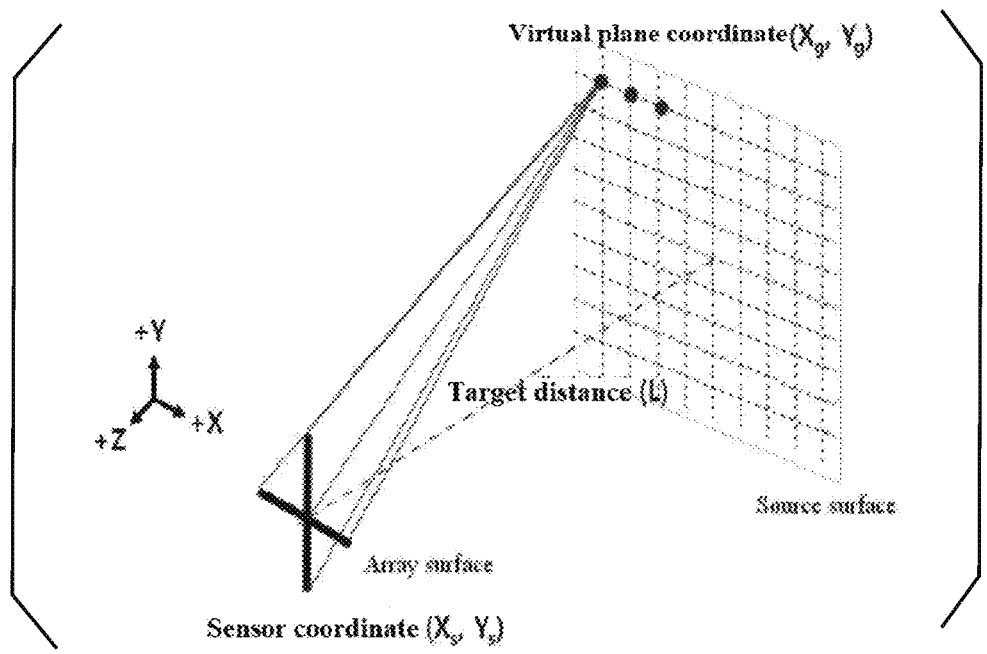
FIG. 1 is a conceptual view of a radiation ultrasonic wave visualization sensor coordinate and a virtual plane coordinate according to the present invention.

Hereinafter, a mobile ultrasonic facility failure diagnosis device having an electronic means and a computer program for visualizing radiation ultrasonic waves will be described in detail with reference to the accompanying drawings.

The present invention relates to a portable ultrasonic facilities diagnosis device used for diagnosing a facility failure by not analyzing an echo-reflected ultrasonic wave with an ultrasonic wave transmitter and an ultrasonic wave receiver but showing a generation location of an ultrasonic wave (not an echo signal) naturally radiated from a machine or facility or a gas pipe as an image and further, showing the ultrasonic wave generation location in one screen through an image and the thermal image.

The portable ultrasonic facilities diagnosis device having an electronic means and a computer program for visualizing radiation ultrasonic waves according to the exemplary embodiment of the present invention includes an ultrasonic sensor array 10, a data acquisition board (DAQ board) 20, a main board 30, a data storage medium 40, a battery 50, a plastic body case 60, a display device 70, an optical camera 80, and an IR camera 90.

Figure 3:
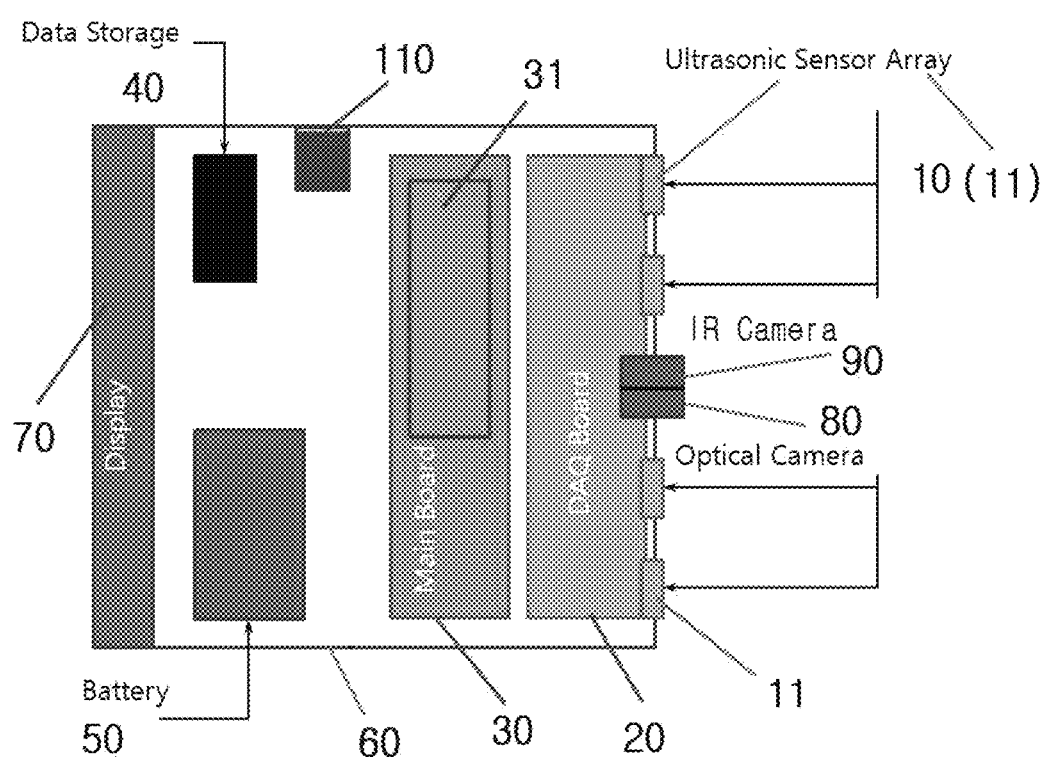
FIG. 3 is a configuration diagram of a mobile ultrasonic facility failure diagnosis device according to the present disclosure.
Figure 4:
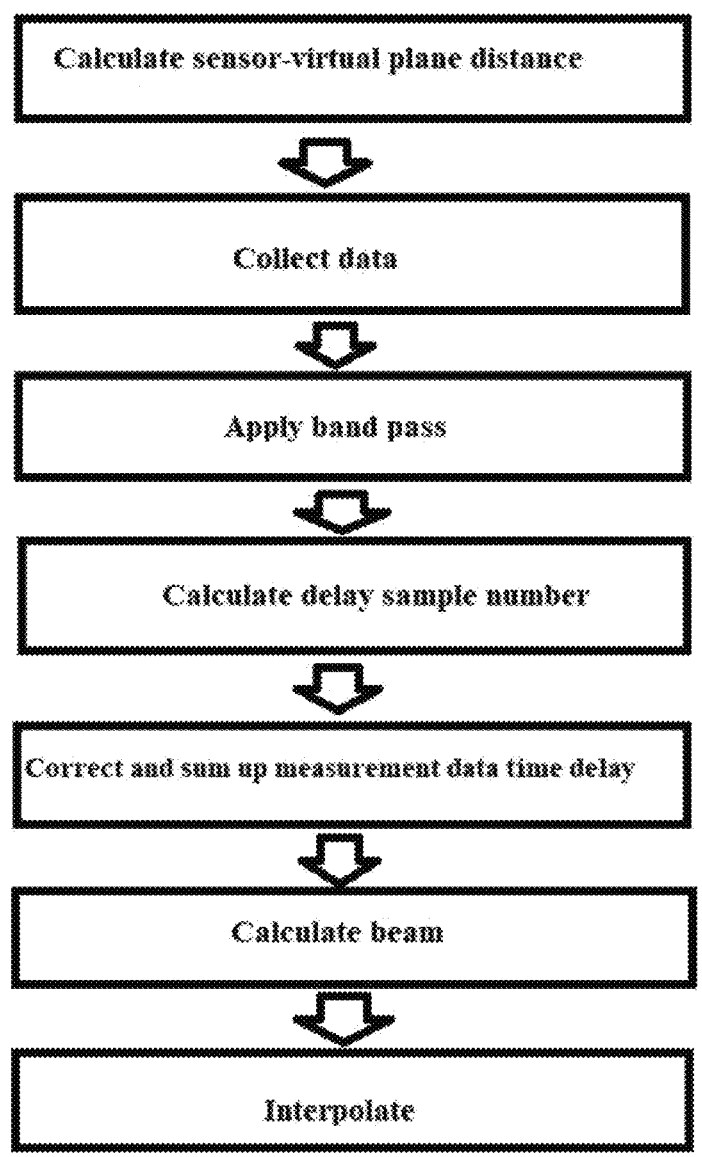
FIGS. 4 and 5 are explanatory diagrams of a radiation ultrasonic wave visualization process according to the present invention.

As illustrated in FIG. 3, the ultrasonic sensor array 10 includes a plurality of (N) ultrasonic sensors 11 and senses ultrasonic signals radiated from a facility while orienting a radiation sound source. The ultrasonic sensor array 10 may have a structure in which a plurality of MEMS microphones, ultrasonic transducers or ultrasonic sensors are mounted on a printed circuit board (PCB) on a planar surface or a flexible PCB on a curved surface.

An electronic circuit for acquiring the ultrasonic signals $x_n$ at a sampling frequency $f_s$ of the ultrasonic signals sensed by the ultrasonic sensor array 10 is mounted on a substrate of the data acquisition board (DAQ board) 20. The data acquisition board (DAQ board) 20 may be responsible for sampling and may incorporate a signal amplification circuit.

The main board 30 has an arithmetic processing unit 31 for processing a digital (or analog) ultrasonic signal received from the data acquisition board (DAQ board) 20 mounted on the substrate thereof and transfers the processed ultrasonic sound source information into the display device 70. The data storage medium 40 stores data processed by the arithmetic processing unit 31 of the main board 30.

The battery 50 supplies power to the data acquisition board 20 and the main board 30. It is preferable that the battery 50 is detachably installed inside the plastic body case 60, but may be a separate portable rechargeable battery that is positioned outside the plastic body case 60 to supply the power to the data acquisition board 20, the main board 30, and the display device 70 by electric wires. Alternatively, both an internal battery and an external auxiliary battery may be provided and used.

The plastic body case 60 is made of a hard material for fixing the ultrasonic sensor array 10, the data acquisition board 20, the main board 30, and the data storage medium 40.

The plastic body case 60 supports the array 10 constituted by the plurality of ultrasonic sensors 11 electrically connected to each other or preferably supports the ultrasonic sensor array 10 by supporting and fixing a PCB board of the ultrasonic sensor array on a flat or curved plate on which the ultrasonic sensors 11 are mounted. A hollow chamber is formed in the plastic body case 60 and the data acquisition board 20 and the main board 30 having an arithmetic processing capability are fixedly installed in the hollow chamber.

The display device 70 visually displays the data processed by the operation processing unit 31 of the main board 30 and is integrally installed in the plastic body case 60. Alternatively, the display device 70 is integrally fixed to the plastic body case 60 so as to be exposed to the outside of the plastic body case 60.

The optical camera 80 picks up an image of a direction in which the ultrasonic sensor array 10 is directed and transmits the image to the main board 30. When the sensor array 10 is has a plat shape, an optical lens of the optical camera 80 is exposed to a direction in which the sensor array 10 is directed. A front surface of the plastic body case 60 has a hole for exposing the lens of the optical camera 80.

The IR camera 90 which picks up the image picks up the thermal image in which the optical camera 80 is directed and transmits the picked-up thermal image to the main board 30 having the operation processing device. The main board 30 overlays and displays the thermal image together with the optical image which is picked up by the optical camera 70 and in the direction in which the sensor array 10 is directed. The IR camera 90 may be substituted with a thermal image pick-up camera having a different thermal pick-up principle.

<Main Board Function>

Figure 5:
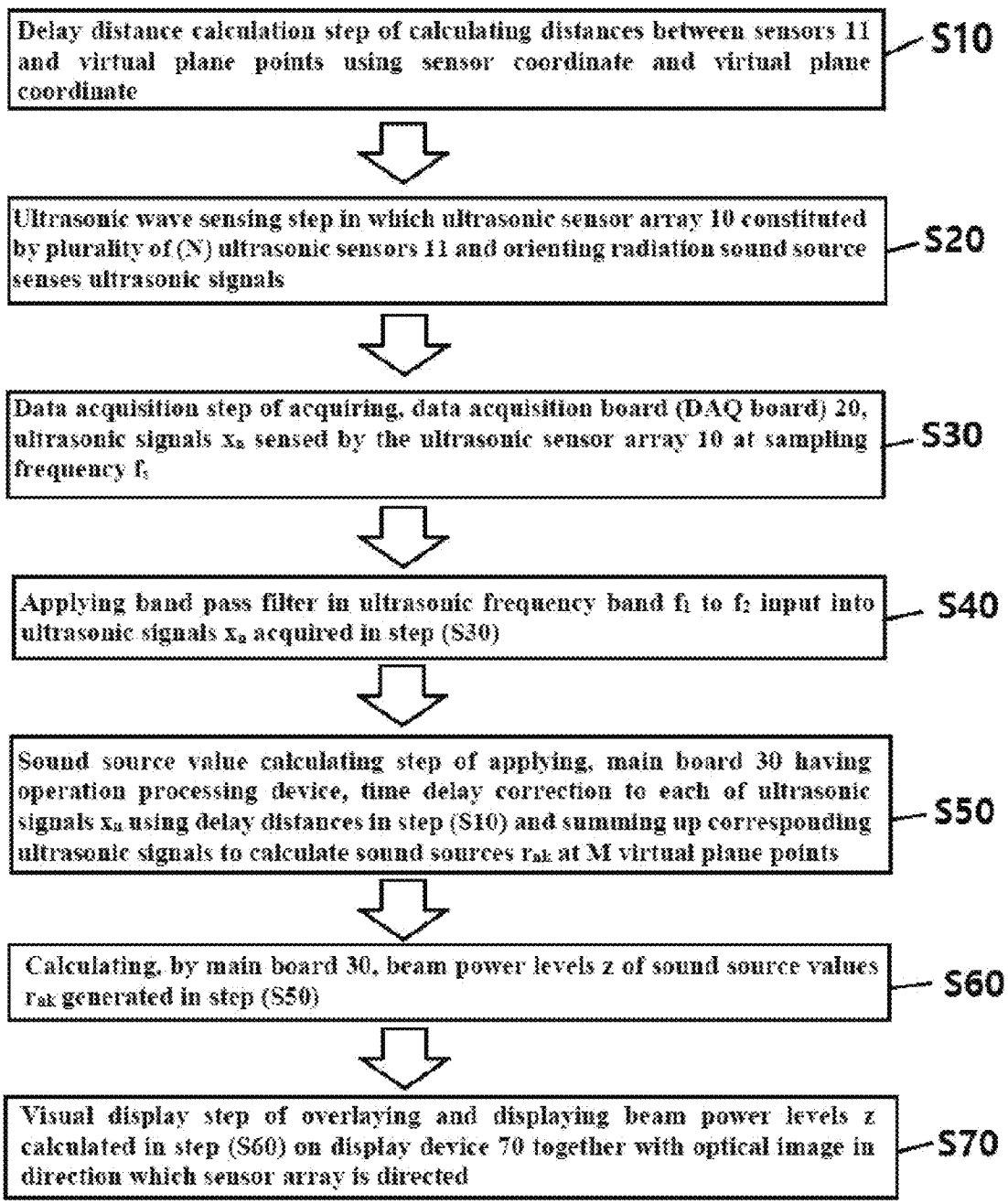

FIG. 5 is a flowchart of a radiation ultrasonic wave visualization method according to the present invention. As illustrated in FIGS. 1 to 5, first, in a delay distance calculation step S10, distances between the sensors 11 and virtual plane points are calculated using a sensor coordinates and a virtual plane coordinate.

FIG. 1 is a diagram illustrating a relationship between a sensor coordinate and a virtual plane coordinate. As illustrated, the distance $d_k$ between the sensor coordinate (Xs, Ys) and the virtual plane coordinate (Xg, Yg) is calculated as follows. When a distance L is 1 m, an operation of $+L^2$ is expressed by +1 operation.

$$d_k = \sqrt{(X_s - X_g)^2 + (Y_s - Y_g)^2 + L^2}$$

Next, in an ultrasonic wave sensing step (S20), the ultrasonic sensor array 10 constituted by the plurality of (N) ultrasonic sensors 11 and orienting the radiation sound source senses the ultrasonic signals.

In a data acquisition step (S30), the data acquisition board (DAQ board) 20 acquires the ultrasonic signals $x_n$ at a sampling frequency $f_s$ of the ultrasonic signals sensed by the ultrasonic sensor array 10. A detailed equation for the ultrasonic signal $x_n$ is as follow.

$$x_n[s] = \sum_{s=0}^{S-1} x_n(t) \cdot \delta\left(t - \frac{S}{f_s}\right)$$

Herein, S represents a sample number. $f_s$ represents sampling Rate (frequency).

After the data acquisition step (S30), a step (S40) is performed, in which a band pass filter of a predetermined ultrasonic frequency band f1 to f2 is applied to the ultrasonic signals $x_n$ acquired in the step (S30) by the main board 30 having the arithmetic processing device. In filtering data $x_{nf}[s]$, $1 \leq nf \leq N$.

$$x_{nf}[s] = x_n[s] \cdot F[s]$$

Figure 2:
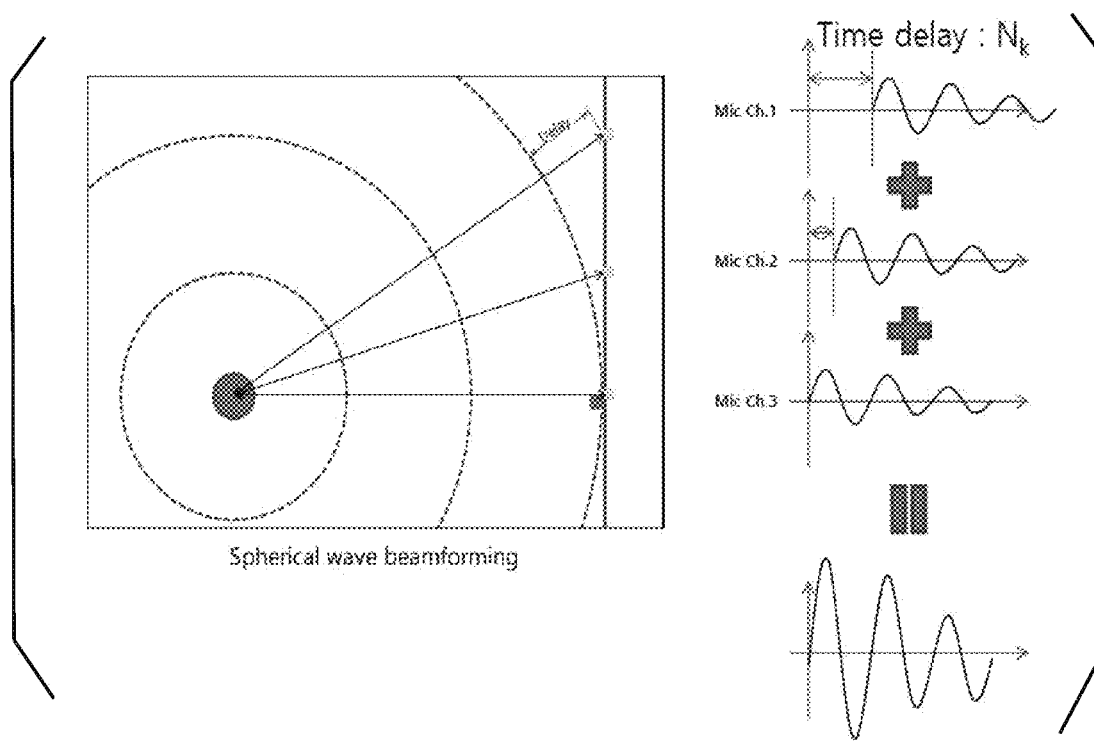
FIG. 2 is a conceptual view of a radiation ultrasonic wave visualization time delay summation according to the present invention.

FIG. 2 is a conceptual view of a radiation ultrasonic wave visualization time delay summation according to the present invention. In a sound source value calculating step (S50) which is performed next, time delay correction is applied to each of the ultrasonic signals $x_n$ by using the delay distances of the step (S10) and the ultrasonic signals to which the time delay correction is applied are aggregated to calculate sound source values $r_{nk}$ off M virtual plane points.

First, a delay sample number is calculated. The time delay is calculated using the distance between the sensor aid the virtual plane and a sound speed and the delay sample number is calculated by the calculated time delay. The details are as follows.

$$\tau_k = \frac{d_k}{C} \text{ (Time delay)},$$
$$N_k = f_s \cdot \tau_k = f_s \cdot \frac{d_k}{C} = \frac{f_s}{C} \cdot d_k = C_d \cdot d_k$$
$$C_d = \frac{f_s}{C}$$

Herein, $C_d$ represents a time delay coefficient and c is the sound speed. $N_k$ represents the delay sample number.

Next, the time delay is compensated by using the delay sample number and summed up. In this case, a correction coefficient for each sensor is applied.

$$\check{r}_{nk}[s] = \sum_{n=0}^{N-1} \alpha_n \cdot x_{nf}[s] \cdot \delta[s - N_k]$$

$\alpha_n$: Weighting Factor

Herein, 1≤nk≤M. M represents the number of all elements in rows and columns on the virtual plane coordinate.

Next, Next, the beam power level calculating step (S60) of calculating the beam power levels z of the generated sound source values $r_{nk}$ is performed.

$$z_k = \frac{1}{N} \sum_{S=0}^{S-1} \check{r}_{nk}^2[s]$$

In the visual display step (S70), the beam power levels z calculated in step 250 are overlayed and displayed on the display device 70 together with an optical image in the direction which the sensor array 10 faces.

<Sensor Array and Sampling Frequency>

As illustrated in FIG. 3, the ultrasonic sensor array 10 may be configured in a structure in which the plurality of ultrasonic sensors 11 is mounted on a printed circuit board forming one plane. The ultrasonic sensor array 10 is exposed in front of the device and arranged in a forward direction (one direction). Alternatively, the plurality of ultrasonic sensors 11 may be arranged at regular intervals on a sphere, a substantially ball-shaped polyhedron, a hemisphere, and a rear opening convex curved body. The ultrasonic sensor array 10 may have a structure in which a plurality of MEMS microphones, ultrasonic transducers or ultrasonic sensors are mounted on a flexible PCB on a curved surface.

Herein, the sampling frequency $f_s$ is in a range of 20 KHz (40 KHz) to 200 KHz (400 KHz) and an upperlimit f1 and a lowerlimit f2 of the ultrasonic frequency band of the band pass filter is preferably in one range which exists between 10 KHz (20 KHz) to 100 KHz.

As a result of testing, it can be known that it is possible to obtain ultrasonic source location information that is effective and required for detection performance of the ultrasonic sensor currently released and diagnosing and monitoring mechanical breakdown, rotation machine breakdown, gas leakage of a gas pipe, and a power facility in this area and further, a data throughput may be appropriately reduced in this area. If the sampling frequency is too large, more data processing is needed, and if the sampling frequency is too small, the ultrasonic area sound source information is lost.

<Band Pass and Hetero Audible Conversion>

The portable facility failure diagnosis device having the electronic means and the computer program for visualizing the radiation ultrasound waves according to the exemplary embodiment of the present invention preferably further includes a sound output means (80, speaker) for sounding. Herein, the main board 30 performs Heterodyne conversion of some or all of the generated sound source values $r_{nk}$ to convert audible sound signals of a sound wave band (100 Hz to 20 KHz) and the main board 30 transmits the audible sound signal to an audible sound output means 90 to allow the user to perceive the radiation ultrasonic wave by auditory sense.

Further, the portable ultrasonic imaging facility diagnosis device includes an input window for a user interface which is electromagnetically connected with the main board 30 so as to be exposed to the plastic body case 60 and the upperlimit $f_1$ and the lowerlimit $f_2$ of the ultrasonic frequency band of the band pass filter may be preferably input through the input window for the user interface by the user. That is, before the ultrasonic wave sensing step S20, a step in which the lowerlimit $f_1$ and the upperlimit $f_2$ of the ultrasonic frequency band of the band pass filter are input through the input window is performed. The step may be performed when the user inputs the upperlimit and the lowerlimit through the input window or the user selects the upperlimit and the lowerlimit among various ranges previously input by a designer.

The present invention has been described in association with the above-mentioned preferred embedment, but the scope of the present invention is not limited to the embodiment and the scope of the present invention is determined by the appended claims, and thereafter, the scope of the present invention will includes various modifications and transformations included in an equivalent range to the present invention.

Reference numerals disclosed in the appended claims are just used to assist appreciation of the present invention and it is revealed that the reference numerals do not influence analysis of the claims and it should not be narrowly analyzed by the disclosed reference numerals.

What is claimed is:

1. A portable device for diagnosing failure of a target instrument by detecting ultrasonic waves from the target instrument and by visualizing the ultrasonic waves on a display of the portable device, wherein the target instrument is a failing machine, a failed facility or a leaking gas pipe, which generates the ultrasonic waves, the portable device comprises:

an ultrasonic sensor array having ultrasonic sensors each sensing ultrasonic signals radiated in form of the ultrasonic waves from the target instrument which serves as an ultrasonic sound source;

a data acquisition board (DAQ board) for acquiring the ultrasonic signals at a sampling frequency;

a main board having an operation processor that processes the ultrasonic signals received from the DAQ board into a visualized image on the display, wherein the DAQ board and the main board are adjacent and engaged to each other in the portable device;

a non-transitory data storage medium for storing the visualized image from the operation processor;

an optical camera for detecting and transmitting an optical image of the ultrasonic sound source to the main board, wherein the optical camera is disposed in the portable device; and the display for displaying the visualized image and the optical image from the main board, wherein the optical image and the visualized image are displayed in overlap with each other on the display, wherein the visualized image is implemented by an operation program embedded and executed in the operation processor, wherein the operation program performs a distance delay calculation by calculating respective distances between the ultrasonic sensors and virtual plane points of the radiation sound source, applies time delay corrections to each of the ultrasonic signals using the distance delay calculation, and generates sound source values serving as the visualized image for each of the virtual plane points by summing the time delay corrections and by calculating beam power levels of the sound source values.

2. The portable device of claim 1, further comprising:

an infrared (IR) camera for picking up a thermal image from the radiation sound source and transmitting the thermal image to the main board, wherein the IR camera is provided adjacent to the optical camera, wherein the thermal image, the optical image and the visualized image are displayed in overlap with each other on the display.

3. The portable device of claim 1, wherein the processor of the main board processes the ultrasonic signals utilizing a band pass filter in predetermined frequency bands.

4. The portable device of claim 3, wherein the band pass filter filters in a range between 10 KHz and 100 KHz.

5. The portable device of claim 1, wherein the ultrasonic sensor array has a shape in which the plurality of ultrasonic sensors are positioned on a single plane.

6. The portable device of claim 1, wherein the sampling frequency is in a range of 20 KHz to 200 KHz.

7. The portable device of claim 1, further comprising:

a charging battery for supplying power to the data acquisition board, the main board, and the display device; and a plastic body case for housing the ultrasonic sensor array, the data acquisition board, the main board, and the data storage medium.

8. The portable device of claim 1, further comprising a speaker, wherein the processor of the main board performs Heterodyne conversion of the sound source values into an audible sound signal, and wherein the processor of the main board transmits the audible sound signal to the speaker to allow a user to perceive the ultrasonic waves from the sound source by an auditory sense.

9. The portable device of claim 1, wherein the ultrasonic sensors are arranged on a sphere at regular intervals.

* * * * *